United States Patent
Barsoum et al.

(10) Patent No.: US 7,534,424 B2
(45) Date of Patent: May 19, 2009

(54) METHOD OF ENHANCING DELIVERY OF A THERAPEUTIC NUCLEIC ACID

(75) Inventors: James G. Barsoum, Lexington, MA (US); Michael Parr, Cambridge, MA (US); Stephen E. Fawell, Framingham, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 10/618,299

(22) Filed: Jul. 11, 2003

(65) Prior Publication Data

US 2004/0086486 A1    May 6, 2004

Related U.S. Application Data

(63) Continuation of application No. PCT/US02/01797, filed on Jan. 22, 2002.

(60) Provisional application No. 60/263,416, filed on Jan. 22, 2001.

(51) Int. Cl.
*A01N 63/00* (2006.01)
*A01N 65/00* (2006.01)
*C12N 15/00* (2006.01)
*C12N 5/00* (2006.01)
*C12N 5/02* (2006.01)

(52) U.S. Cl. ............... 424/93.1; 424/93.21; 435/320.1; 435/325

(58) Field of Classification Search ............ 514/44, 514/252.12; 424/93.1; 435/320.1
See application file for complete search history.

(56) References Cited

U.S. PATENT DOCUMENTS

| | | | |
|---|---|---|---|
| 3,710,795 A | 1/1973 | Higuchi et al. | 128/260 |
| 4,797,368 A | 1/1989 | Carter et al. | 435/320 |
| 5,262,564 A | 11/1993 | Kun et al. | 562/430 |
| 5,399,346 A | 3/1995 | Anderson et al. | 424/93.21 |
| 6,025,195 A * | 2/2000 | Sandig et al. | 435/320.1 |
| 6,696,423 B1 | 2/2004 | Barsoum et al. | |
| 2003/0229042 A1 | 12/2003 | Barsoum et al. | |

FOREIGN PATENT DOCUMENTS

WO    WO 99/10516    3/1999
WO    WO 01/60377    8/2001

OTHER PUBLICATIONS

Ghosh, et al., "Liver-directed gene therapy: promises, problems and prospects at the turn of the century" (2000) J. Hepatol., 32(Suppl. 1): 238-52.*
Telesnitsky, et al., "Reverse Transcriptase and the Generation of Retroviral DNA" (1997) Retroviruses, Ed. by Coffin, et al., Cold Spring Laboratory Press, Plainview, NY., pp. 128-129.*
Shenk, "Adenoviridae: The Viruses and Their Replication" (2001) Fundamental Virology, 4th Ed., Ed. by Knipe, et al., Lippincott, Williams and Wilkins, New York, NY., p. 1054.*
Olsnes, et al. "Ricin" (2001) Toxicon, 39: 1723-28.*
Rooijen, et al. (1996) Hepatology, 23(5): 1239-43.*
van Til, et al. (2005) Molec. Therap., 11(1): 26-34.*
R. Alemany, et al., "Blood Clearance Rates of Adenovirus Type 5 in Mice," *Journal of General Virology*, 81(11):2605-9 (2000).
D. Armentano et al., "Effect of the E4 Region on the Persistence of Transgene Expression from Adenovirus Vectors," *Journal of Virology*, 71(3):2408-16 (1997).
N. B. Beck, et al., "Baculovirus Vectors Repress Phenobarbital-Mediated Gene Induction and Stimulate Cytokine Expression in Primary Cultures of Rat Hepatocytes," *Gene Therapy*, 7(15):1274-83 (2000).
C. A. Bradham, et al., "Activiation of Nuclear Factor-KappaB During Orthotopic Liver Transplantation in Rats is Protective and Does Not Require Kupffer Cells," *Liver Transplantation and Surgery*, 5(4):282-93 (1999).
H. Chao, et al., "Several Log Increase in Therapeutic Transgene Delivery by Distinct Adeno-Associated Viral Serotype Vectors," *Molecular Therapy*, 2(6):619-623 (2000).
H. Chen, et al. "Persistence in Muscle of an Adenoviral Vector that Lacks All Viral Genes," *Proceedings of the National Academy of Sciences U.S.A.*, 94:1645-1650 (1997).
T. Daemen, et al., "Liposomal Doxorubicin-Induced Toxicity: Depletion and Impairment of Phagocytic Activity of Liver Macrophages," *International Journal of Cancer*, 61(5):716-721 (1995).
H. J. Delecluse, et al., "The Genetic Approach to the Epstein-Barr Virus: From Basic Virology to Gene Therapy," *Molecular Pathology*, 53(5):270-9 (2000).
O. Devergne, et al., "In Vivo Expression of IL-1 Beta and IL-6 Genes During Viral Infections in Human," *European Cytokine Network*, 2(3):183-94 (1991).

(Continued)

*Primary Examiner*—Robert M Kelly
(74) *Attorney, Agent, or Firm*—Sterne, Kessler, Goldstein & Fox P.L.L.C.

(57) ABSTRACT

The invention provides methods and compositions for increasing the delivery of nucleic acids into a host by administering a nucleic acid encoding a therapeutic nucleic acid along with an agent that modulates Kupffer cell function in the host.

11 Claims, 5 Drawing Sheets

OTHER PUBLICATIONS

K. E. Drazan, et al., "Viral IL-10 Gene Therapy Inhibits TNF-Alpha and IL-1 Beta, Not IL-6, in the Newborn Endotoxemic Mouse," *Journal of Pediatric Surgery*, 31(3):411-4, (1996).

J. F. Engelhardt, et al., "Prolonged Transgene Expression in Cotton Rat Lung with Recombinant Adenoviruses Defective in E2a," *Human Gene Therapy*, 5 (10):1217-29 (1994).

J. L. Goldstein, et al., "Defective Lipoprotein Receptors and Atherosclerosis. Lessons From an Animal Counterpart of Familial Hypercholesterolemia," *New England Journal of Medicine*, 309(5):288-96 (1983).

S. Hegenbarth, et al., "Liver Sinusoidal Endothelial Cells Are Not Permissive for Adenovirus Type 5," *Human Gene Therapy*, 11(3):481-6 (2000).

W. S. Hu, et al., "Design of Retroviral Vectors and Helper Cells for Gene Therapy," *Pharmacological Reviews*, 52(4):493-511 (2000).

S. Ishibashi, et al., "Hypercholesterolemia in Low Density Lipoprotein Receptor Knockout Mice and Its Reversal by Adenovirus-Meidated Gene Delivery," *Journal of Clinical Investigation*, 92(2):883-93 (1993).

S. Ishibashi, et al., "Massive Xanthomatosis and Atherosclerosis in Cholesterol-Fed Low Density Lipoprotein Receptor-Negative Mice," *Journal of Clinical Investigation*, 93(5):1885-93 (1994).

K. Jooss, et al., "Cyclophosphamide Diminishes Inflammation and Prolongs Transgene Expression Following Delivery of Adenoviral Vectors to Mouse Liver and Lung," *Human Gene Therapy*, 7(13):1555-66 (1996).

K. Jooss, et al., "Blunting of Immune Responses to Adenoviral Vectors in Mouse Liver and Lung with CTLA4Ig," *Gene Therapy*, 5(3): 309-319 (1998).

M. A. Kay, et al., "Transient Immunomodulation with anti-CD40 Ligand Antibody and CTLA4Ig Enhances Persistence and Secondary Adenovirus-Mediated Gene Transfer into Mouse Liver," *Proceedings of the National Academy of Sciences U. S. A.*, 94: 4686-4691 (1997).

M. A. Kay, et al., "Viral Vectors for Gene Therapy: The Art of Turning Infectious Agents Into Vehicles of Therapeutics," *Nature Medicine*, 7(1):33-40 (2001).

N. Kuriyama, et al., "Pretreatment with Protease is a Useful Experimental Strategy for Enhancing Adenovirus-Mediated Cancer Gene Therapy," *Human Gene Therapy*, 11(16):2219-30 (2000).

A. Lieber, et al., "The Role of Kupffer Cell Activation and Viral Gene Expression in Early Liver Toxicity after Infusion of Recombinant Adenovirus Vectors," *Journal of Virology*, 71(11):8798-8807 (1997).

A. Lieber, et al., "Inhibition of NF-KappaB Activation in Combination with Bcl-2 Expression Allows for Persistence of First-Generation Adenovirus Vectors in the Mouse Liver," *Journal of Virology*, 72 (11):9267-77 (1998).

S. Longman, et al., "Accumulation of Protein-Coated Liposomes in an Extravascular Site: Influence of Increasing Carrier Circulation Lifetimes," *Journal of Pharmacology and Experimental Therapeutics*, 275(3):1177-1184 (1995).

N. Morral, et al., "High Doses of a Helper-Dependent Adenoviral Vector Yield Supraphysiological Levels of Alpha1-Antitrypsin with Negligible Toxicity," *Human Gene Therapy*, 9(18):2709-16 (1998).

X. Q. Qin, et al. "Interferon-β Gene Therapy Inhibits Tumor Formation and Causes Regression of Established Tumors in Immune-Deficient Mice," *Proceedings of the National Academy of Sciences U. S. A.*, 95:14411-14416 (1998).

M. J. Parr, et al., "The Presence of $G_{-M1}$ in Liposomes with Entrapped Doxorubicin Does Not Prevent RES Blockade," *Biochimica et Biophysica Acta*, 1168(2):249-252 (1993).

G. Schieder, et al., "Genomic DNA Transfer with a High-Capacity Adenovirus Vector Results in Improved In Vivo Gene Expression and Decreased Toxicity," *Nature Genetics*, 18(2):180-3 (1998).

W. M. Siders, et al., "T Cell- and NK Cell-Independent Inhibition of Hepatic Metastases by Systemic Administration of an IL-12-Expressing Recombinant Adenovirus," *The Journal of Immunology*, 160:5465-5474 (1998).

N. Somia and I. M. Verma, "Gene Therapy: Trials and Tribulations," *Nature Reviews Genetics*, 1(2):91-9 (2000).

K. Tanzawa, et al., "WHHL-Rabbit: A Low Density Lipoprotein Receptor-Deficient Animal Model For Familial Hypercholesterolemia," *FEBS Letters*, 118(1):81-4 (1980).

N. Tao, et al., "Sequestration of Adenoviral Vector by Kupffer Cells Leads to a Nonlinear Dose Response of Transduction in Liver," *Molecular Therapy: The Journal of the American Society of Gene Therapy*, 3(1):28-35 (2001).

W. M. Tsui, et al., "Liver Changes in Reactive Haemophagocytic Syndrome," *Liver*, 12(6):363-7 (1992).

V. W. van Beusechem, et al., "Recombinant Adenovirus Vectors with Knobless Fibers for Targeted Gene Transfer," *Gene Therapy*, 7 (22):1940-6 (2000).

N. van Rooijen, et al., "Transient Suppression of Macrophage Functions by Liposome-Encapsulated Drugs," *Trends in Biotechnology*, 15(5):178-185 (1997).

S. Wang, et al., "Effect of Clodronate on Macrophage Depletion and Adenoviral-Mediated Transgene Expression in Salivary Glands," *Journal of Oral Pathology and Medicine*, 28(4):145-51 (1999).

J. M. Wilson, et al., "Cystic Fibrosis. Vehicles for Gene Therapy." *Nature*, 365(6448):691-2 (1993).

G. Wolff, et al., "Enhancement of In Vivo Adenovirus-Mediated Gene Transfer and Expression by Prior Depletion of Tissue Macrophages in the Target Organ," *Journal of Virology*, 71(1):624-9 (1997).

Brunner, K.R., et al., "Blood Clearance of $P_{32}$-Labeled Vesicular Stomatitis and NewCastle Disease Viruses by the Reticuloendothelial System in Mice," *J. Immunol.*, 85:99-105, American Association of Immunologists (1960).

Cai, P., et al., "Methyl palmitate: Inhibitor of phagocytosis in primary rat Kupffer cells," *Toxicol.* 210:197-204, Elsevier Ireland Ltd. (Jun. 2005), Dachs, G.U., et al., "Targeting Gene Therapy to Cancer: a Review," *Oncol. Res.* 9:313-325, Cognizant Communication Corporation (1997).

Fahimi, H.D., "The Fine Structural Localization of Endogenous and Exogenous Peroxidase Activity in Kupffer Cells of Rat Liver," *J. Cell. Biol.* 47:247-262, Rockefeller University Press (1970).

Kirn, A., et al., "Uptake of Viruses by Kupffer Cells Isolated from Human Liver," *Lancet North Am. Ed.* 2:585-586, Lancet Publishing Group (1980).

Kolb-Bachofen, V., "Uptake of Toxic Silica Particles by Isolated Rat Liver Macrophages (Kupffer Cells) Is Receptor Mediated and Can Be Blocked by Competition," *J. Clin. Invest.* 90:1819-1824, The American Society for Clinical Investigation, Inc. (1992).

Laurent, N., et al., "Uptake by rat liver and intracellular fate of plasmid DNA complexed with poly-$_L$-lysine or poly-$_D$-lysine," *FEBS Lett.* 443:61-65, Federation of European Biochemical Societies (1999).

Kuzmin, A.I., et al., "Macrophage depletion increases the safety, efficacy and persistence of adenovirus-mediated gene transfer in vivo," *Gene Ther.* 4:309-316, Stockton Press (1997).

Marianneau, P., et al., "Infection of Primary Cultures of Human Kupffer Cells by Dengue Virus: No Viral Progeny Synthesis, but Cytokine Production Is Evident," *J. Virol.* 73:5201-5206, American Society for Microbiology (1999).

McCuskey, R.S., et al., "Kupffer Cell Function in Host Defense," *Rev. Infect. Dis.* 9:S616-S619, The University of Chicago (1987).

Miller, N., and Vile, R., "Targeted vectors for gene therapy," *FASEB J.* 9:190-199, The Federation of American Societies for Experimental Biology (1995).

Mogensen, S.C., "Macrophages and Age-Dependent Resistance to Hepatitis Induced by Herpes Simplex Virus Type 2 in Mice," *Infect. Immun.* 19:46-50, American Society for Microbiology (1978).

Rentsch, M., et al., "Benefit of Kupffer cell modulation with glycine versus Kupffer cell depletion after liver transplantation in the rat: effects on postischemic reperfusion injury, apoptotic cell death graft regeneration and survival," *Transpl. Int.* 18:1079-1089, European Society for Organ Transplantation (Sep. 2005).

Rubin, D.H., et al., "Transport of Infectious Reovirus into Bile: Class II Major Histocompatibility Antigen-Bearing Cells Determine Reovirus Transport," *J. Virol* 61:3222-3226, American Society for Microbiology (1987).

Selgrade, M.K., and Osborn, J.E., "Role of Macrophages in Resistance to Murine Cytomegalovirus," *Infect. Immun. 10*:1383-1390, American Society for Microbiology (1974).

van Til, N.P., et al., "Kupffer Celler and Not Liver Sinusoidal Endothelial Cells Prevent Lentiviral Transduction of Hepatocytes," *Mol. Ther. 11*:26-34, The American Society for Gene Therapy (Jan. 2005).

Wake, K., et al., "Cell Biology and Kinetics of Kupffer Cells in the Liver," *Int. Rev. Cytol. 118*:173-229, Academic Press, Inc. (1989).

Zenilman, M.E., et al., "Use of Ricin A-Chain to Selectively Deplete Kupffer Cells," *J. Surg. Res. 45*:82-89, Academic Press, Inc. (1988).

Leissner, P., et al., "Influence of adenoviral fiber mutations on viral encapsidation, infectivity and in vivo tropism," *Gene Ther. 8*:49-57, Nature Publishing Group (Jan. 2001).

Kadowaki, S., et al., Prevention of genetic resistance to bone marrow allografts by reticuloendothelial system blockade, *Biomed & Pharmacother 45*:417-422, Elsevier Science Ltd. (1991).

Kadowaki, S., et al., Applicaiton of poly(L-lactic acid) particles for the suppression of genetic resistance to bone marrow allografts by reticuloendothelial system-blockade, *Biomed & Pharmacother 47*:385-391, Elsevier Science Ltd. (1993).

\* cited by examiner

METHOD OF ENHANCING DELIVERY OF A THERAPEUTIC NUCLEIC ACID

This application is a continuation of PCT International application number PCT/US02/01797, filed Jan. 22, 2002, which claims benefit of U.S. provisional application No. 60/263,416, filed Jan. 22, 2001. The disclosures of International application PCT/US02/01797 and U.S. provisional application 60/263,416 are incorporated by reference herein.

FIELD OF THE INVENTION

The invention relates to methods and compositions for enhancing the delivery of nucleic acids into a host and more specifically to methods and compositions for enhancing the delivery and expression of virally encoded transgenes into a host.

BACKGROUND

Adenoviral vectors, including replication-defective adenoviral vectors, are being used as gene delivery vehicles for a wide range of transgenes in pre-clinical and clinical studies across many pathological indications. Intravenous administration of recombinant adenoviral vectors results in the transduction of hepatocytes, expression of the encoded transgenes and detectable circulating levels of secreted transgene products.

Delivery of low amounts of recombinant adenoviral particles can lead to low or undetectable levels of an encoded transgene product. Delivery of large amounts of adenoviral particles containing a therapeutic nucleic acid can result in high levels of the expressed transgene. High expression levels of adenovirus particles containing a therapeutic transgene can lead to complications such as liver toxicity. Therefore, there is a need in the art for better control of transgene expression in subjects treated with recombinant viral vectors.

SUMMARY OF THE INVENTION

The invention is based in part on the discovery that small increases in the dose of an adenovirus encoding human interferon-beta ("IFN-β") can lead to large, i.e., non-linear, increases in the amount of the encoded human IFN-β. In contrast, transgene expression after administering a single low doses of an adenovirus encoding human IFN-β in mice is dramatically increased by co-administering a recombinant adenovirus lacking human IFN-β, when comparing it to the same viral dose with no co-administered "empty" recombinant virus. The enhancement of IFN-β transgene expression is also observed in mice that have been treated with liposomal doxorubicin, which is known to deplete liver macrophages known as Kupffer cells. Accordingly, the invention provides methods and compositions for optimizing the dosage of a therapeutic nucleic acid such as a therapeutic nucleic acid provided in a viral vector, such as an adenovirus vector.

While not wishing to be bound by theory, it is believed that delivery of low doses of adenoviruses in a subject results in preferential uptake of the adenoviruses by the subject's Kupffer cells. The Kupffer cells sequester the low doses of viruses without expressing the transgene and present a blockade to viral transduction. Once this blockade is saturated, efficient gene delivery of a virally-encoded therapeutic gene product (such as IFN-β) to the subject can be achieved. Therefore, a therapeutic nucleic acid provided in, e.g., a viral vector, such as an adenovirus vector, can be efficiently delivered to the subject if administered with an agent that saturates the viral uptake capacity of Kupffer cells, or by lowering levels of Kupffer cells. In one embodiment, the delivery is intravenous delivery. In addition, the subject comprises cells capable of expressing the transgene.

Accordingly, in one aspect the invention features a method for increasing the level of a therapeutic gene product, such as a virally-encoded therapeutic gene product, in a subject by administering to the subject a therapeutic nucleic acid encoding the therapeutic gene product and an agent that modulates Kupffer cell function in the subject; in some embodiments, a viral vector, such as an adenovirus vector, comprises said therapeutic nucleic acid; in some embodiments, said viral vector comprising said therapeutic nucleic acid is provided in viral particle, such as an adenovirus particle.

In one embodiment, the saturating agent is a recombinant viral particle. In another embodiment, the saturating agent is particulate matter. In some embodiments, the agent modulates Kupffer cell function by lowering levels of Kupffer cells in the subject. An example of this type of agent is liposomal doxorubicin.

In some embodiments, the Kupffer cell function modulated by the agent is uptake, e.g., phagocytosis, of a particle that includes the therapeutic nucleic acid by a Kupffer cell. In other embodiments, the Kupffer cell function that is modulated by the agent is receptor-mediated uptake by a Kupffer cell of a particle that includes the therapeutic nucleic acid. An example of an agent that is taken up by a Kupffer cell is a viral particle that does not include the therapeutic nucleic acid.

In some embodiments, the agent can be provided as a viral nucleic acid, e.g., a viral nucleic acid that lacks the therapeutic nucleic acid, or lacks a nucleic acid encoding a functional copy of the therapeutic nucleic acid. In other embodiments, the agent is of a size that is suitable for phagocytic uptake by the Kupffer cells of a subject. In further embodiments, the agent that is taken up by a Kupffer cell is particulate matter whose component particles have a diameter of about 10 nm to about 1000 nm. In particular embodiments, the particulate matter is about the same diameter as the viral vector encoding the therapeutic transgene product.

In some embodiments, the agent is administered prior to the administering of the therapeutic nucleic acid. For example, the agent can be administered less than 24 hours, less than 10 hours, less than 8 hours, less than 4 hours, less than 2 hours, less than 1 hour, and less than 10 minutes prior to administering the therapeutic nucleic acid. In other embodiments, the agent is administered less than 5 minutes prior to administering the therapeutic nucleic acid. In some embodiments, a viral vector, such as an adenovirus vector, comprises said therapeutic nucleic acid; in some embodiments, said viral vector comprising said therapeutic nucleic acid is provided in viral particle, such as an adenovirus particle.

In other embodiments, the agent is administered concurrently with the therapeutic nucleic acid. In some embodiments, a viral vector, such as an adenovirus vector, comprises said therapeutic nucleic acid; in some embodiments, said viral vector comprising said therapeutic nucleic acid is provided in viral particle, such as an adenovirus particle.

In other embodiments, the agent is administered concurrently with the therapeutic nucleic acid or prior to the administering of the therapeutic nucleic acid, but not after the administering of the therapeutic nucleic acid. In some embodiments, a viral vector, such as an adenovirus vector, comprises said therapeutic nucleic acid; in some embodiments, said viral vector comprising said therapeutic nucleic acid is provided in viral particle, such as an adenovirus particle.

The therapeutic nucleic acid, or the agent, or both can be administered to the subject by any route known in the art. For example, the therapeutic nucleic acid and agent can be administered via oral, nasal, parenteral, transdermal, topical, intraocular, intratracheal, intraperitoneal, direct injection into cells, tissue, organ or tumor, intravenous, subcutaneous, or intramuscular delivery. In certain embodiments, intravenous administration includes administration via the portal vein or by hepatic artery infusion.

In certain embodiments, the virally encoded nucleic acid is provided in an adenovirus.

In another aspect, the invention features a method for increasing levels of a virally-encoded therapeutic gene product in a hepatocyte cell population. The method includes contacting the hepatocyte cell population with a therapeutic nucleic acid encoding the therapeutic gene product and an agent that modulates Kupffer cell function in the subject. One of the Kupffer cell functions that is being modulated is the uptake of the agent. Uptake of the agent may be nonspecific, such as through phagocytosis, or may be specific, such as through receptor mediated uptake.

In a further aspect, the invention provides a method of modulating toxicity (e.g., hepatotoxicitity) associated with a virally encoded transgene by administering to a subject in need thereof an agent that modulates Kupffer cell function in the subject. In some embodiments, the agent is administered prior to administration of a therapeutic nucleic acid encoding the therapeutic gene product. In other embodiments, the agent is administered concurrently with administration of a therapeutic nucleic acid encoding the therapeutic gene product. A therapeutic gene product encoded by the nucleic acid may be a polypeptide, an antisense nucleic acid, or an antibody.

Also provided by the invention is a method for modulating expression in liver of high levels, (e.g., toxic levels) of a therapeutic protein by administering to a subject in need of gene therapy at least one dose of a viral vector lacking a polynucleotide for expression of the therapeutic gene product either prior to or concurrent with administering at least one dose of a viral vector containing a polynucleotide for expression of the therapeutic gene product. In some embodiments, the levels of the therapeutic gene product correspond to the levels of therapeutic nucleic acid so administered.

Also provided by the invention is a pharmaceutical composition comprising a viral nucleic acid encoding a therapeutic gene product, an agent that modulates Kupffer cell function, and a pharmaceutically acceptable carrier.

The invention provides methods and compositions that allow for a near linear correlation between viral dose and expression of a therapeutic gene product encoded by the nucleic acid. The methods and compositions of the invention also allow for minimization of the toxic effects associated with the viral proteins or expression of the encoded therapeutic gene product.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION

The invention provides methods for improving the delivery of nucleic acids encoding therapeutic gene products (e.g., virally-encoded therapeutic gene products) by delivering the nucleic acids in conjunction with an agent that negatively affects Kupffer cell function in the subject.

In general, the method can be used to deliver any therapeutic nucleic acid to the subject. Examples of therapeutic nucleic acids include nucleic acids encoding polypeptides, antisense nucleic acids, nucleic acids encoding ribozymes, and nucleic acids encoding components of a spliceosome. When therapeutic nucleic acids encode polypeptides, the encoded polypeptide can be, e.g., a cytokine such as interferon-alpha, interferon-beta, or interferon-gamma, interleukins, growth factors such as erythropoietin, human growth hormone, insulin, granulocyte colony stimulating factor ("G-

CSF"), granulocyte-macrophage colony stimulating factor ("GM-CSF") and clotting factors such as factor VIII and factor IX.

In certain embodiments, the therapeutic nucleic acid is provided in a vector that allows for encapsulation of the gene of the encoded therapeutic product into a particle. In certain embodiments the particle can be taken-up by a Kupffer cell. A suitable particle is a viral particle, e.g., an adenovirus particle.

Any method known in the art for the insertion of polynucleotide sequences into a vector may be used. Such methods are described in, e.g., Sambrook et al., 1989 *Molecular Cloning: a Laboratory Manual*, Cold Spring Harbor Laboratory, Cold Spring Harbor, N.Y. and Ausubel et al., 1992 *Current Protocols in Molecular Biology*, J. Wiley & Sons, NY, both of which are incorporated herein by reference. Vectors may include appropriate transcriptional and translational control signals operatively linked to the polynucleotide sequence for a particular therapeutic gene. Promoters and enhancers may also be used to control expression of therapeutic proteins or gene products. Promoter activation may be tissue specific or inducible by a metabolic product or administered substance. Such promoters and enhancers include, but are not limited to, the native E2 F promoter, the cytomegalovirus immediate-early promoter and enhancer (Karasuyama et al., 1989 *J. Exp. Med.*, 169: 13); the human beta-actin promoter (Gunning et al., 1987 *Proc. Nat. Acad. Sci. USA*, 84: 4831); the glucocorticoid-inducible promoter present in the mouse mammary tumor virus long terminal repeat (MMTV LTR) (Klessig et al., 1984 *Mol. Cell. Biol.*, 4: 1354); the long terminal repeat sequences of Moloney murine leukemia virus (MuLV LTR) (Weiss et al., 1985 *RNA Tumor Viruses*, Cold Spring Harbor Laboratory, Cold Spring Harbor, N.Y.); the SV40 early region promoter (Bernoist and Chambon, 1981 *Nature*, 290: 304); the promoter of the Rous sarcoma virus (RSV) (Yamamoto et al., 1980 *Cell*, 22: 787); the herpes simplex virus (HSV) thymidine kinase promoter (Wagner et al., 1981 *Proc. Nat. Acad. Sci. USA*, 78: 1441); the adenovirus promoter (Yamada et al., 1985 *Proc. Nat. Acad Sci. USA*, 82: 3567).

Specific viral vectors for use in gene transfer systems are now well established. See for example: Madzak et al., *J. Gen. Virol.*, 73: 1533-36 (1992: papovavirus SV40); Moss et al., *Curr. Top. Microbiol. Immunol.*, 158: 25-38 (1992: vaccinia virus); Margulskee, *Curr. Top. Microbiol. Immunol.*, 158: 67-93 (1992: herpes simplex virus (HSV) and Epstein-Barr virus (EBV)); Miller, *Curr. Top. Microbiol. Immunol.*, 158: 1-24 (1992: retrovirus); Brandyopadhyay et al., *Mol. Cell. Biol.*, 4: 749-754 (1984: retrovirus); Miller et al., *Nature*, 357: 455-450 (1992: retrovirus); Anderson, *Science*, 256: 808-813 (1992: retrovirus), herpes viruses (for example, herpes simplex virus based vectors), and parvoviruses (for example, "defective" or non-autonomous parvovirus based vectors), and all of which are incorporated herein by reference. In various embodiments, recombinant viral vectors designed for use in gene therapy are used in the invention. See, e.g., Hu and Pathak 2000 *Pharmacol Rev*. 52: 493-512; Somia and Verma 2000 *Nature Rev*. 1: 91-99; van Beusechem et al., 2000 *Gene Ther*. 7: 1940-1946; Glorioso et al., 2001 *Nature Med*. 7: 33-40. Additionally, viral vectors may be administered in combination with transient immunosuppressive or immunomodulatory therapies. See, e.g., Jooss et al., 1996 *Hum Gene Ther*. 7: 1555-1566; Kay et al., *Pro. Nat. Acad. Sci. USA* 94: 4686-4691.

In certain embodiments, the specific viral type used is the same for both the viral vector containing the therapeutic gene product and for the viral vector agent that does not contain the therapeutic gene product. Any or all of the viral vectors may be replication-defective.

In other embodiments, viral serotypes, e.g., the general adenovirus types 2 and 5 (Ad2 and Ad5, respectively), may be administered on an alternating dosage schedule where multiple treatment will be administered. Specific dosage regimens may be administered over the course of several days, when an immune response against the viral vector is anticipated, or both. In nonlimiting examples of specific embodiments, Ad5-based viral vectors may be used on day 1, Ad2-based viral vectors may be used on day 2, or vice versa.

In some embodiments, therapeutic nucleic acids are additionally provided in replication-defective recombinant viruses or viral vectors. These can be generated in packaging cell lines that produce only replication-defective viruses. See, e.g., *Current Protocols in Molecular Biology*: Sections 9.10-9.14 eds. Ausubel et al., 1989 Greene Publishing Associates.

Adenovirus Vectors

In some embodiments, a vector for delivering a therapeutic nucleic acid is an adenovirus-based vector. See, e.g., Berkner et al., *Curr. Top. Microbiol. Immunol.*, 158: 39-61 (1992). In some embodiments, the adenovirus-based vector is an Ad-2 or Ad-5 based vector. See, e.g., Muzyczka, *Curr. Top. Microbiol. Immunol.*, 158: 97-123, 1992; Ali et al., 1994 *Gene Therapy* 1: 367-384; U.S. Pat. Nos. 4,797,368 and 5,399,346.

Adenoviruses can be modified to efficiently deliver a therapeutic or reporter transgene to a variety of cell types. For example, the general adenoviruses types 2 and 5 (Ad2 and Ad5, respectively), which cause respiratory disease in humans, are currently being developed for clinical trials, including treatment of cancer or other cell proliferation diseases and disorders, and for gene therapy of Duchenne Muscular Dystrophy (DMD) and Cystic Fibrosis (CF). Both Ad2 and Ad5 belong to a subclass of adenovirus that are not associated with human malignancies. Adenovirus vectors are capable of providing high levels of transgene delivery to diverse cell types, regardless of the mitotic 25 state of the cell. High titers ($10^{13}$ plaque forming units/ml) of recombinant virus can be easily generated in 293 cells (an adenovirus-transformed, complementation human embryonic kidney cell line: ATCC No. CRL1573) and cryo-stored for extended periods without appreciable losses. The efficacy of this system in delivering a therapeutic transgene in vivo that complements a genetic imbalance has been demonstrated in animal models of various disorders. See, e.g., Watanabe, 1986 *Atherosclerosis*, 36: 261-268; Tanzawa et al., 1980 *FEBS Letters*, 118(1): 81-84; Golasten et al., 1983 *New Engl. J. Med.*, 309: 288-296; Ishibashi et al., 1993 *J. Clin. Invest.*, 92: 883-893; Ishibashi et al., 1994 *J. Clin. Invest.*, 93: 1889-1893, all of which are incorporated herein by reference. Recombinant replication defective adenovirus encoding a cDNA for the cystic fibrosis transmembrane regulator (CFTR) gene product has been approved for use in at least two human CF clinical trials. See, e.g., Wilson, 1993 *Nature*, 365: 691-692.

Some replication-deficient adenoviruses which have been developed for clinical trials contain deletions of the entire E1a and part of the E1b regions. This replication-defective virus is grown in 293 cells containing a functional adenovirus E1a gene which provides a transacting E1a protein. E1-deleted viruses are capable of replicating and producing infectious virus in the certain cells (e.g., 293 cells), which provide E1a and E1b region gene products in trans. The resulting virus is capable of infecting many cell types and can express the introduced gene (providing it carries its own promoter). However, the virus cannot replicate in a cell that does not carry the E1 region DNA unless the cell is infected at a very high multiplicity of infection. Other adenoviral vectors developed for clinical trials may be used in the invention. Examples include Ad vectors with recombinant fiber proteins for modified tropism (e.g., van Beusechem et al., 2000 *Gene Ther*. 7: 1940-1946), protease pre-treated viral vectors (e.g., Kuriyama et al., 2000 *Hum. Gene Ther*. 11: 2219-2230), E2a temperature sensitive mutant Ad vectors (e.g., Engelhardt et al., 1994 *Hum. Gene Ther*. 5: 1217-1229), and "gutless" Ad vectors (e.g., Armentano et al., 1997 *J. Virol*. 71: 2408-2416; Chen et al., 1997 *Proc. Nat. Acad. Sci. USA* 94: 1645-1650; Schieder et al., 1998 *Nature Genetics* 18: 180-183).

Adenoviruses have a broad host range, can infect quiescent or terminally differentiated cells such as neurons, and appear to be essentially non-oncogenic. Adenoviruses additionally do not appear to integrate into the host genome. Because they exist extrachromasomally, the risk of insertional mutagenesis is greatly reduced. See, e.g., Ali et al. 1994, supra, at 373. Recombinant adenoviruses (rAdV) produce very high titers, the viral particles are moderately stable, expression levels are high, and a wide range of cells can be infected.

Adeno-associated viruses (AAV) have also been used as vectors for somatic gene therapy. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep 62 and rep 40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene. See, e.g., Carter, In *Handbook of Parvoviruses*, ed., Tijsser, CRC Press, pp. 155-168 (1990). It has been shown that the ITRs represent the minimal sequence required for replication, rescue, packaging, and integration of the AAV genome.

In alternative embodiments, the agent modulates Kupffer cell function by lowering levels of Kupffer cells in the subject. An example of this type of agent is liposomal doxorubicin.

In some embodiments, the Kupffer cell function is modulated by an agent that is taken up by the Kupffer cell instead of a viral particle containing the therapeutic nucleic acid. An example of an agent that is phagocytosed by a Kupffer cell is a viral particle (such as an adenovirus particle) that lacks the therapeutic nucleic acid. The viral particle may lack the therapeutic nucleic acid completely, or alternatively, may include a variant of the therapeutic nucleic acid that does not encode a functional protein. In some embodiments, it is desirable to include a viral transgene that encodes a readily detectable marker protein, such as β-galactosidase.

A further example of an agent that is phagocytosed by a Kupffer cell is particulate matter, wherein the particulate matter includes particles that have a diameter of about 10 nm to about 1000 nm. In particular embodiments, the particles are about the same diameter as the viral vector being administered to a subject and which encodes the therapeutic transgene product. In some embodiments, particles making up the particulate matter may be composed of an organic component, an inorganic components, or a combination of both. In further embodiments, component particles of the particulate matter may be either biodegradable or resistant to in viva degradation. In some embodiments, component particles themselves elicit little or no biological activity in the subject being treated. Use of any type and composition of materials utilized by persons skilled in the art for uptake by Kupffer cells is contemplated by the invention.

In some embodiments, the nucleic acid encoding the therapeutic gene product could be provided as part of a viral particle. Thus, a nucleic acid containing viral regulatory regions and encoding structural proteins, as well as the therapeutic nucleic acid, can be used to produce virus particles, which are then introduced to the subject. In some embodiments, the nucleic acid is introduced directly into the subject.

In general the agent is administered prior to delivery of the therapeutic nucleic acid. Alternatively, the agent is administered concurrently with the therapeutic nucleic acid. For example, the agent can be administered less than 24 hours, less than 10 hours, less than 8 hours, less than 4 hours, less than 2 hours, less than 1 hour, less than 10 minutes, and even less than 5 minutes prior to administering the therapeutic nucleic acid. In other embodiments, the agent is administered less than five minutes prior to administering the therapeutic nucleic acid.

The subject in the above-mentioned methods can be any animal for which introduction of a foreign nucleic acid is desired. Thus, the subject can include, e.g., mammals, reptiles or birds. Specific examples include a human, mouse, rat, dog, cat, horse, cow, pig, or non-human primate. Administration can be systemic or topical, and can be prophylactic or therapeutic.

Also provided by the invention is a method for modulating delivery of a virally encoded transgene to a subject. In the method a dosage inflection point is identified for a virus containing the virally encoded transgene in the subject. As used herein, a "dosage inflection point" is a point at which a small incremental change in the amount of virus delivered to the subject results in a substantial change in the amount of viral gene product. The inflection point is compared to levels of the virally encoded gene product in the subject. The dose of the virus containing the transgene is then adjusted, if necessary, to deliver an appropriate amount of viral nucleic acid that results in the desired dose of the virally encoded transgene.

Pharmaceutical Compositions

The invention also includes at least one pharmaceutical composition comprising a viral nucleic acid encoding a therapeutic gene product, an agent that modulates Kupffer cell function, and a pharmaceutically acceptable carrier. The viral nucleic acid can be provided as part of a viral particle, if desired. In some embodiments, the pharmaceutical composition is provided in a pharmaceutically effective amount. The term "pharmacologically or pharmaceutically effective amount" means that amount of a drug or pharmaceutical agent that will elicit the biological or medical response of a tissue, system, animal or human that is being sought by a researcher or clinician.

In some embodiments, the compositions are suitable for internal use and include an effective amount of a pharmacologically active compound of the invention, alone or in combination, with one or more pharmaceutically acceptable carriers. The compounds are especially useful in that they have very low, if any, toxicity.

The compounds herein described can form the active ingredient of a pharmaceutical composition, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like. The compositions typically will include an effective amount of active compound or the pharmaceutically acceptable salt thereof, and in addition, and may also include any carrier materials as are customarily used in the pharmaceutical sciences. Depending on the intended mode of administration, the compositions may be in solid, semi-solid or liquid dosage form, such as, for example, injectables, tablets, suppositories, pills, time-release capsules, powders, liquids, suspensions, or the like, for example, in unit dosages.

Administration of the active compounds and salts described herein can be via any of the accepted modes of administration for therapeutic agents. These methods include systemic or local administration such as oral, nasal, parenteral, transdermal, subcutaneous, or topical administration modes.

For instance, for oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, alginic acid or its sodium salt, or effervescent mixtures, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixers, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are, for example, aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference in its entirety.

Furthermore, certain compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. In some embodiments, other topical preparations include creams, ointments, lotions, aerosol sprays and gels, wherein the concentration of active ingredient would range from 0.1% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

Compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as, for example, sodium acetate, triethanolamine oleate, etc.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Compounds of the present invention may be administered in a single dose. Alternatively, compounds of the invention may be administered in a single daily dose, or the total daily dosage may be administered in divided doses of two, three or four times daily. Additionally, compounds of the invention may be administered over the course of several days or weeks. Dosing regimens for administration of therapeutics are well known to persons skilled in the art.

Any of the above pharmaceutical compositions may contain 0.1-99%, 1-70%, or 1-50% of the active compounds of the invention as active ingredients.

The compounds of the present invention may be administered with another therapeutic agent, as one or more pharmaceutical compositions. The other therapeutic agent may be administered prior to, concurrently with or after the administration of the compounds of the present invention. The other therapeutic agent may be, for example, a therapeutic agent known in the art for that particular indication.

Throughout this specification and claims, the word "comprise," or variations such as "comprises" or "comprising," will be understood to imply the inclusion of a stated integer or group of integers but not the exclusion of any other integer or group of integers.

EXAMPLES

The invention will be illustrated in the following non-limiting examples.

Example 1

Injection of Mice with Adenovirus Particles Containing a Reporter Nucleic Acid Along with Adenovirus Particles Containing Human Interferon-Beta Nucleic Acid Results in Enhanced Expression of Human Interferon-beta The effect of administration of adenovirus particles containing a reporter nucleic acid along with adenoviral particles containing human interferon-beta nucleic acid on circulating IFN-β levels was examined.

Adenoviral Vectors

The E1-deleted, E2a-temperature-sensitive adenoviruses H5.110CMVhIFN-β and H5.110CMVlacZ encode human IFN-β and β-galactosidase, respectively, driven by the cytomegalovirus (CMV) early promoter. See, e.g., Qin, et al. 1998 *Proc. Natl. Acad. Sci., USA* 95: 14411-14416. The E1, E3-deleted adenoviruses H5.010CMVhα1AT and H5.010CMVlacZ encode human α 1-antitrypsin ("α1AT") and β-galactosidase ("lacZ"), respectively, also driven by CMV early promoter. See, e.g., Jooss, et al. 1998 *Gene Ther.* 5: 309-319. All virus preparations were highly purified by two rounds of cesium chloride banding and particle titers were determined as previously described. See, e.g., Nyberg-Hoffman, et al. 1997 *Nat. Med.* 3: 808-811; Chardonnet and Dales, 1970 *Virology* 40: 462-477.

Groups of five mice (C57BL/6, Balb/c, C3H, NCR nude, C57BL/J6 rag-1 mice, or Balb/c nu/nu as specified) were injected intravenously ("i.v.") via the tail vein with various doses of recombinant adenoviruses in 100 μl phosphate buffered saline ("PBS") in all experiments. Doses and virus constructs were as described below. Blood was obtained on day 1 for α1AT and day 3 for hIFN-β assays by tail vein bleeding or cardiac puncture, sera were prepared and samples were stored at –80° C. To study the biodistribution of adenovirus following tail vein injection, $1 \times 10^{10}$, $3 \times 10^{10}$, $10 \times 10^{10}$ and $30 \times 10^{10}$ particles of Cy3-labeled H5.010CMVeGFP virus were injected in nine C57BL/6 mice per group. As a control, 100 μl of fluorophore Cy3 ($2 \times 10^{13}$) was injected into two animals. Animals were sacrificed to harvest liver, spleen, lung, and kidney tissues at 30 minute, 4 hour and 24 hour post vector injection. The animals from the control group were harvested at 30 minutes only.

For the animal study using β-galactosidase as the reporter, mice were sacrificed 3 days following administration of H5.110CMVlacZ and the livers extracted in whole lobes. The liver tissue was briefly washed in PBS, then fixed for 4 hours in 4% paraformaldehyde/PBS containing 2 mM magnesium chloride ($MgCl_2$) at 4° C. Tissues were washed overnight in PBS/2 mM $MgCl_2$ at 4° C., then sliced into 2 mm thick sections. These thick sections were then washed again overnight in PBS/2 mM $MgCl_2$ at 4° C., then stained with X-gal (1 mg/ml 5-bromo-4-chloro-3-indolyl-β-D-galactopyranoside in 5 mM each potassium ferricyanide and potassium ferrocyanide in wash buffer above) for 4 hours at 37° C. Tissues were washed briefly again, photographed, then paraffin embedded, sectioned (10 μm) and stained for Kupffer cells using the F4-80 antibody, as described below. Sections were counter-stained with nuclear fast red.

Interferon-beta levels were quantitated by use of an ELISA assay. Ninety-six-well plates were coated overnight at 4° C. with an anti-human IFN-β antibody, (BO-2; Summit Pharmaceuticals, Fort Lee, N.J.). The antibody was used at 10 μg/ml in the coating buffer containing 50 mM sodium bicarbonate/carbonate, 0.2 mM $MgCl_2$, and 0.2 mM $CaCl_2$ (pH 9.6). After the plates were blocked with 0.5% non-fat dry milk in PBS for 1 hr at room temperature, IFN-β samples or IFN-β protein standards (AVONEX™, Biogen), diluted in 10% normal mouse serum, 0.5% non-fat dry milk, 0.05% Tween-20 in PBS, were then added. After capture for 1.5 hr at room temperature, the plates were washed and successively incubated at room temperature for 1 hr with an anti-IFN-β rabbit sera (Biogen sample #447, 1:2,000 dilution), washed again, and then incubated 1 hr with horseradish peroxidase ("HRP")-conjugated donkey anti-rabbit antibody (Jackson ImmunoResearch, 1:5,000 dilution). Following a final wash, substrate solution (4.2 mM tetramethylbenzidine, 0.1 M sodium acetate-citric acid, pH 4.9) was then added. The reaction was stopped by the addition of 2 M hydrogen persulfate ("$H_2SO_4$") and absorbance was measured at 450 nm.

Figure 1:
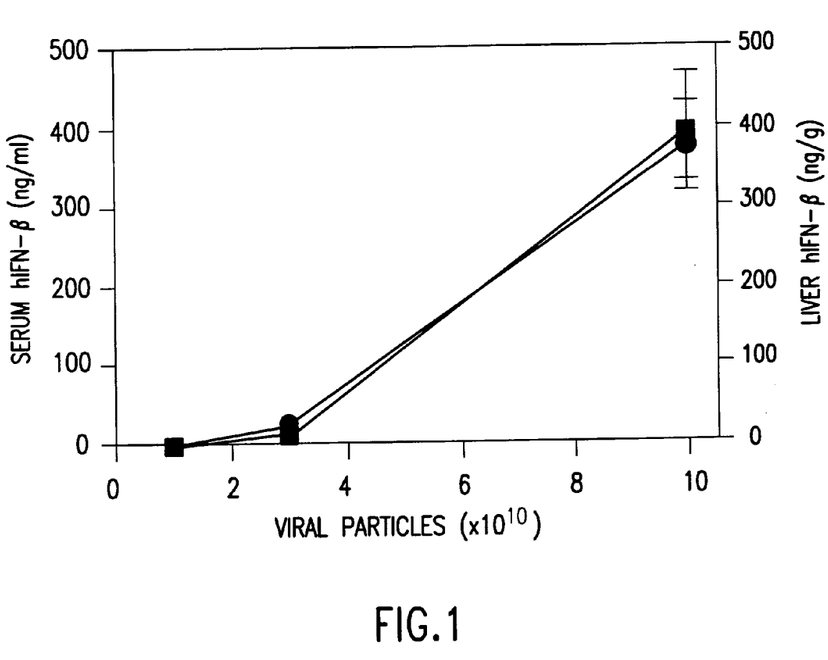
FIG. 1 is a graph depicting the non-linear dose response of hIFN-β expression following intravenous administration of an E1-deleted, E2a-temperature sensitive adenoviral vector expressing human interferon-β ("H5.110CMVhIFN-β").

The E1 deleted, E2a temperature sensitive adenoviral vector expressing human IFN-β (H5.110CMVhIFN-β) was i.v. injected via the tail vein into female Balb/c nude mice (n=5/group). The results are shown in FIG. 1. The concentration of hIFN-β in both sera (■, black square, shown as ng/ml) and liver homogenates (●, black circle, shown as ng/g liver wet weight) was determined by ELISA on day 7. Average serum hIFN-β levels are shown ±SEM.

A non-linear dose response of hIFN-β expression was observed following i.v. administration of H5.110CMVhIFN-β alone. High doses of vector ($1 \times 10^{11}$ particles per mouse) showed disproportionately high expression levels of hIFN-β compared to low doses ($1 \times 10^{10}$ particles). At relatively low levels of virus, namely $1-3 \times 10^{10}$ H5.110CMVhIFN-β viral particles per mouse, only very low levels of IFN-β could be detected in the serum and liver of mice, with peak expression typically between 3 and 7 days post injection.

Increasing the dose to $1 \times 10^{11}$ particles, however, resulted in a disproportionately large increase in IFN-β levels, typically with a 10-100 fold increase in IFN-β levels from only a 3 fold increase in viral dose. This non-linear dose response was not due to retention of IFN-β in the liver at low IFN-β expression levels and secretion into circulation only at high levels of expression, because the non-linear dose response was seen both in IFN-β levels in serum and within liver tissue extracts. A similar non-linear dose response was observed previously; however the basis for this was not determined. See, e.g., Morral, et al. 1998 *Hum. Gene Ther.* 9: 2709-2716; Shirley, et al. 1998 *Blood* 92: 296a.

Figure 2A:
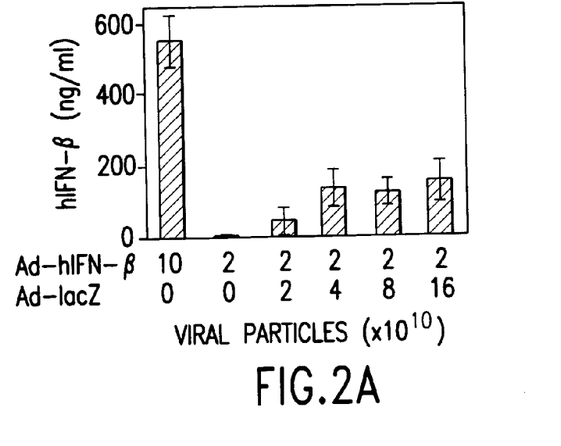
FIG. 2A is a graph showing that co-administration of H5.110CMVlacZ with low doses of H5.110CMVhIFN-β enhances IFN-β expression.

Mice were also injected with either a high dose ($1 \times 10^{11}$ particles) or a low dose ($2 \times 10^{10}$ particles) of H5.110CMVhIFN-β, or a dose comprising a mixture of $2 \times 10^{10}$ particles of H5.110CMVhIFN-β with varying amounts of H5.110CMVlacZ (an equivalent adenovirus that encodes the β-galactosidase gene). The results are shown in FIG. 2A. Again, the difference in IFN-β expression level between the high (serum IFN-β level over 500 ng/ml) and low dose groups (serum IFN-β level of 3.8 ng/ml) was far greater than the difference in viral dose. Remarkably however, co-administration of the lacZ encoding adenovirus dramatically enhanced the resulting IFN-β expression levels. The H5.110CMVlacZ helper adenovirus was titrated to determine the optimal dose needed to give maximal expression of the fixed low dose of $2\times10^{10}$ particles reporter H5.110CMVhIFN-β. Enhanced IFN-β expression was seen at all H5.110CMVlacZ doses with a 10-fold enhancement (40 ng/ml IFN-β) observed with as little as $2\times10^{10}$ particles H5.110CMVlacZ. IFN-β expression reached a plateau at approximately 130 ng/ml with $4\times10^{10}$ particles H5.110CMVlacZ. Thus, with $4\times10^{10}$ particles or greater H5.110CMVlacZ co-treatment, the dose response was more proportionate, with a H5.110CMVhIFN-β dose of $2\times10^{10}$ particles (one-fifth the high dose) resulting in approximately one-quarter the level of IFN-β observed with the $1\times10^{11}$ particles H5.110CMVhIFN-β dose.

These results demonstrate that a non-linear relationship exits between viral dose and an encoded protein produced by the virus. These results also demonstrate that a roughly linear relationship exists between viral dose and an encoded protein produced by the virus can be achieved by administration of an adenovirus vector that does not encode the protein along with a virus encoding the protein.

Example 2

The Dosage Response Observed in Mice with Human IFN-β is not Due to a Biological Effect of Human IFN-β in Mice Since human IFN-β does not have detectable cross-species activity in mice, it is unlikely that human IFN-β has a biological effect in the mouse system. See, e.g., Joklik, 1991 in *Fundamental Virology*, eds. Fields & Knipe (Raven Press, New York), pp. 281-307. However, to exclude this possibility and the possibility that the pharmacokinetics of human IFN-β might be in part responsible for these phenomena, the experiment in Example 1 was repeated using H5.010CMVhα1AT, an E1 and E3 deleted adenovirus expressing the human α1AT cDNA ("hα1AT"), in place of H5.110CMVhIFN-β.

Levels of α1-AT were quantitated by use of an ELISA assay. Ninety-six-well plates were coated overnight at 4° C. with rabbit anti-human α1-antitrypsin ("α1-AT") antibody (Sigma Chemical Co., St. Louis, Mo.) used at 10 mg/ml in coating buffer containing 50 mM sodium bicarbonate/carbonate, pH 9.5. The plates were blocked with 3% BSA for 1 h at room temperature, washed, and incubated with α1-AT protein standards (Sigma Chemical Co.) or serum samples diluted in 0.5% BSA and 0.05% Tween 20 in PBS. Following incubation for 2 h at 37° C. or overnight at 4° C., the plates were incubated at room temperature for 2 h with a 1:5000 dilution of horseradish peroxidase-conjugated goat anti-human α1-AT antibody (EY Laboratories, San Mateo, Calif.). The plates were then incubated at room temperature with peroxidase substrate (Kirkegaard and Perry Laboratories, Gaithersburg, Mass.) and the absorbance was measured at 450 nm within 30 min.

Figure 2B:
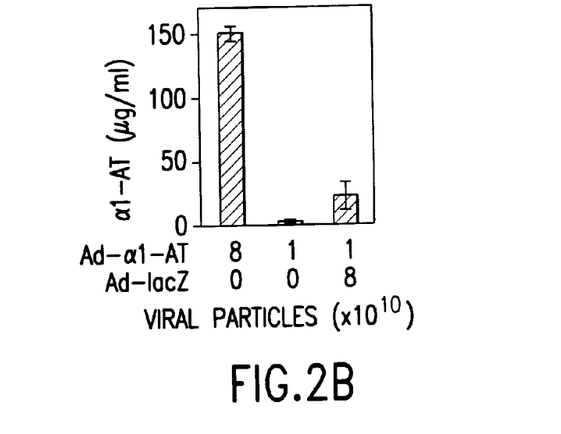
FIG. 2B is a graph depicting the non-linear dose-response with H5.010CMVhα1-AT as the reporter virus.

A non-linear dose response was again observed. The results are shown in FIG. 2B. The low dose of $1\times10^{10}$ particles resulted in serum levels of 2.8 μg/ml α1-AT, while $8\times10^{10}$ particles resulted in serum levels of 152 μg/ml α1-antitrypsin. A low dose of $1\times10^{10}$ particles H5.010CMVhα1AT mixed with $8\times10^{10}$ particles H5.000CBLacZ resulted in levels of 23.8 μg/ml α1-antitrypsin, once again achieving a level close to a linear dose response. Thus, the non-linear dose response and the enhancement by treatment with another adenovirus are not specific to the IFN-β reporter protein. A series of other experiments compared various adenoviral constructs bearing different replication defects (e.g., E1 deleted, E1 deleted and E2a temperature sensitive, and E1 and E4 deleted) as either the reporter virus or the non-reporter virus. The non-linear dose response and enhancement by the non-reporter adenovirus was observed with all three generations of virus, indicating that the degree of defectiveness of these viruses is not a critical parameter underlying this phenomenon. The same results also were obtained when different promoters directing expression of the reporter gene were evaluated.

Example 3

Adenoviruses Encoding LacZ Enhance Adenoviral IFN-β Gene Expression if Administered Prior to or Concurrently with Adenovirus Encoding IFN-β

The effect of varying the dose of an adenovirus encoding lacZ, and the effect of adding the reporter gene adenovirus before or after the adenovirus encoding hIFN-β, was determined.

Dose response experiments and co-administration studies were initially performed on tissue culture cells. The experiments were performed in Huh7 cells using H5.110CMVlacZ as the reporter virus, H5.110CMVhIFN-β as the non-reporter virus and using a luminescent assay for lacZ activity to determine transgene expression levels.

Figure 2C:
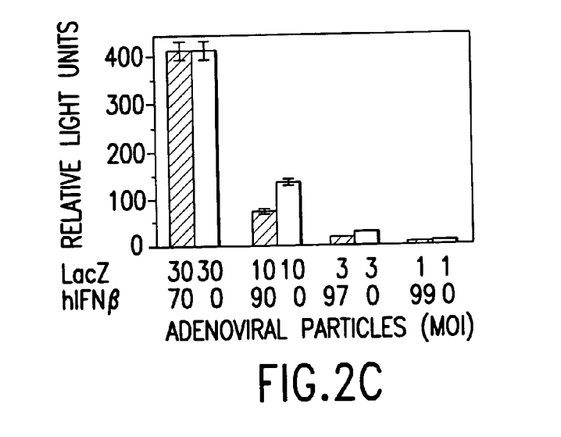
FIG. 2C is a graph depicting the linear dose-response of H5.110CMVlacZ when infecting Huh7 cells in vitro with either H5.110CMVlacZ alone or with a mixture of H5.110CMVlacZ and H5.110CMVhIFN-β at the multiplicity of infection ("MOI") indicated.

The human hepatoma cell line Huh7 (ATCC) was plated in 24-well plates at $7\times10^4$ cells per well. Cells were infected 6-8 hr later with either H5.110CMVlacZ at multiplicity of infection (MOI) of 30, 10, 3 and 1, or with mixtures of H5.110CMVlacZ and H5.110CMVhIFN-β as indicated. Twenty four hours later, cells were lysed in reporter lysis buffer (Promega) and cell debris were removed by brief centrifugation. Cell lysates were incubated with reaction buffer (Clontech) for an hour at room temperature in 96-well plates and the β-galactosidase activities were then measured by luminometer. The results are shown in FIG. 2C.

In all these in vitro experiments, approximately linear dose responses were observed, and no enhancement by non-reporter virus addition was observed. This indicates that the non-linear dose-response is an in vivo phenomenon.

Figure 3:
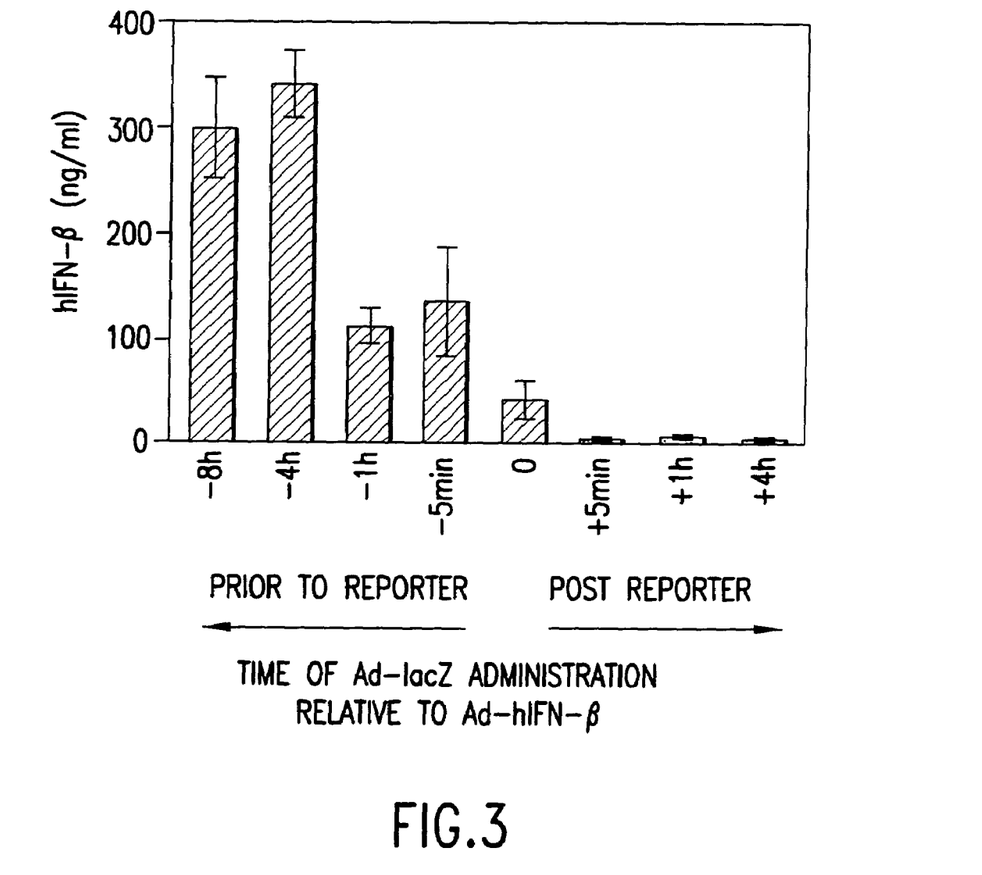
FIG. 3 is a graph depicting the enhanced expression seen when Balb/c nude mice are pretreated with low doses of H5.110CMVhIFN-β pre-administration, but not post-administration, of H5.110CMVlacZ.

The time course of administration of the adenoviruses was next examined in vivo. The two viral preparations described in Example 1 were mixed prior to intravenous injection. Administering the non-reporter virus prior to, or after the injection of the reporter virus was compared. The results are shown in FIG. 3. Injection of H5.110CMVlacZ as little as 5 minutes after the H5.110CMVhIFN-β gave no enhancement of IFN-β serum levels (3-8 ng/ml). If the lacZ virus was increasing IFN-β expression by providing functions needed for replication of the reporter virus, a dramatic effect of this very brief separation in time would not be expected. Consistent with previous data, the adenovirus co-administration resulted in an approximately 10-fold higher IFN-β level (42 ng/ml). Surprisingly, the animals in which H5.110CMVlacZ was administered prior to H5.110CMVhIFN-β had even higher IFN-β expression than the co-administration mice, with 4-8 hr pre-dosing appearing to be optimal and resulting in approximately 300 ng/ml serum IFN-β in this experiment. Increased IFN-β levels were not observed when H5.110CMVlacZ was administered 24-48 hr prior to H5.110CMVhIFN-β (data not shown).

Figure 4:
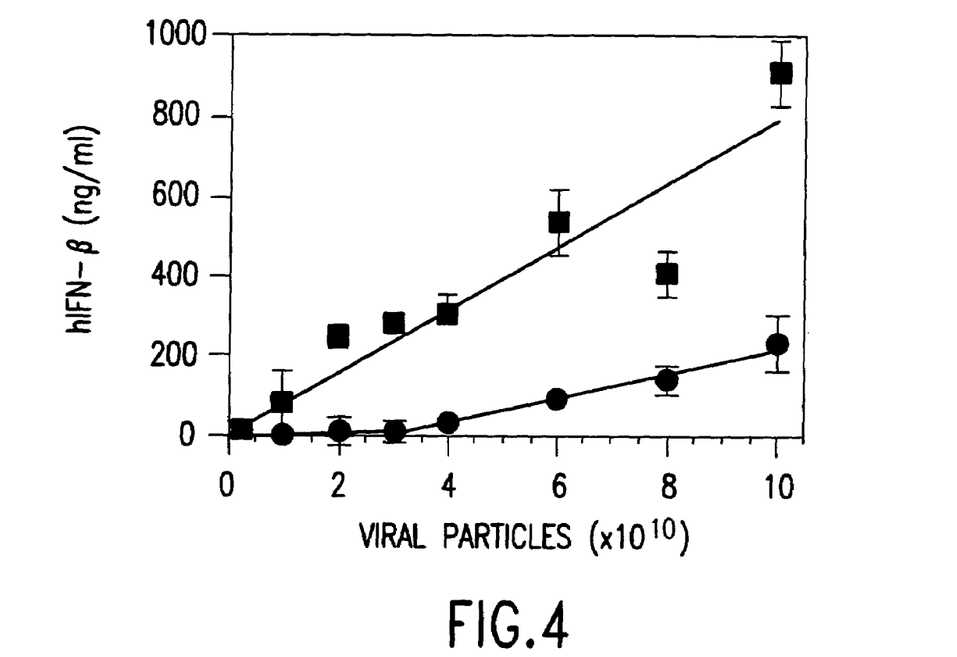
FIG. 4 is a graph depicting the linear relationship between H5.110CMVhIFN-β and serum hIFN-β following pre-dosing with H5.110CMVlacZ.

These experiments were extended to cover full dose-response curves of animals with or without pre-dosing with H5.110CMVlacZ. The results are shown in FIG. 4. Balb/c nude mice were injected with H5.110CMVhIFN-β at doses between $0.3 \times 10^{10}$ and $10 \times 10^{10}$ particles either alone (black circles) or injected four hours following the injection of a saturating dose ($8 \times 10^{10}$ particles) of H5.110CMVlacZ (black squares). Serum concentration of hIFN-β (n=5/group, average±SEM shown) were determined on day 3 by ELISA. As seen previously, while very low doses of H5.110CMVhIFN-β ($0.3$-$3.0 \times 10^{10}$ particles) in the absence of H5.110CMVlacZ pre-treatment led to undetectable to very low serum levels of IFN-β, a non-linear increase in serum IFN-β was seen at $4 \times 10^{10}$ particles and above. When H5.110CMVlacZ pre-dosing was performed, significant IFN-β serum levels were observed following administration of very low doses of H5.110CMVhIFN-β, and the relationship between virus dose and serum IFN-β was roughly linear.

Example 4

Modulation of the Dose-response is not Promoter-dependent

Another possible mechanism to account for these data is cytokine-mediated activation of the viral promoter used to direct expression of the reporter transgene. For example, the pro-inflammatory factor NF-kB can stimulate promoters having NF-kB binding sites. See, e.g., Lieber, et al. 1997 *J. Virol.* 71: 8798-8807; Lieber, et al. 1998 *J. Virol.* 72: 9267-9277. However, similar results were obtained regardless of whether the promoter used either contained or lacked NF-kB binding sites (i.e., the CMV IE promoter and the α1AT promoter, respectively). Taken together with the lack of this effect in vitro, more complex components of the host physiology or immune system likely mediate the effects shown here.

Example 5

Treatment of Mice with Doxorubicin/Liposomes Enhances Expression of a Subsequently Administered Adenovirus hIFN-β Transgene Intravenous administration of various viral gene therapy vectors, and adenovirus in particular, has been reported to target the liver, resulting in efficient injection of hepatocytes and subsequent transgene expression. Intravenous administration has also been reported to result in uptake into the Kupffer cells in the liver.

To verify this observation, fluorescently labeled adenovirus particles were prepared and introduced into mice. To prepare adenovirus with the Cy3 carbocyanine dye covalently conjugated to its capsid proteins, a Cy3 labeling kit was purchased from Amersham Pharmacia Biotech, Arlington Heights, Ill. See, e.g., Leopold, et al. 1998 *Hum. Gene Ther.* 9: 367-378. Highly purified recombinant adenovirus H5.010CMVEGFP stock in PBS was adjusted to a concentration of $5 \times 10^{12}$ particles/ml. One ml of the virus stock was used for the labeling reaction according to the manufacturer's instruction. The free Cy3 dye was removed by dialyzing the reaction mixture in dialysis chamber (6,000-8,000 MW cut-off, Slide-a-lyser, Pierce Chem. Co., Rockford, Ill.) against 4 liters of PBS at 4° C. overnight. Cy3 dye concentration was assayed as instructed by the manufacturer.

Kupffer cells were immunohistochemically labeled using the F4/80 anti-macrophage antibody. Paraffin sections of 5 μm were cut, put on coated slides, cleared and rehydrated. Following equilibration in PBS, sections were treated with 1% hydrogen peroxide ("$H_2O_2$") in methanol, rinsed in PBS, and blocked to prevent nonspecific binding (SuperBlock, Pierce). Kupffer cells were labeled with F4/80 anti-macrophage polyclonal antibody (Serotec) and a biotinylated goat-anti-rat secondary antibody (Ventana Medical Systems). Secondary antibody and avidin-HRP detection (DAB substrate) were carried out using a NexES automated immunostainer (Ventana Medical Systems).

To visualize uptake of Cy3 labeled vector and co-staining of macrophages, blocks of liver tissue were removed 30 minutes post-portal vein injection. The tissue was frozen and embedded in OCT compound (Sakura) for sectioning. Cryosections 8 μm thick were placed on slides, fixed in acetone at −20° C. for 15 minutes and allowed to air dry. Sections were post-fixed in 1× Morpho-Save (Ventana Medical Systems) for 15 minutes and washed in PBS. Macrophages were detected with the anti-macrophage antibody (Serotec, rat anti-mouse, clone F4/80) for 1 hour at room temperature. Slides were washed in PBS, blocked with 10% SuperBlock (Pierce) for 15 minutes at room temperature. Following washing in PBS, the primary antibody was fluorescently labeled with AlexaFluor 488 goat anti-rat antibody (Molecular Probes). Images were taken with a Leitz DMR fluorescent microscope and a SPOT-RT CCD camera, and combined in Image-Pro (Media Cybernetics).

Intravenous injection of fluorescently labeled adenovirus was observed to target liver Kupffer cells, as shown by positive immunostaining in treated liver sections. Low levels of staining were also observed in the spleen and lung. Despite the predominant Kupffer cell uptake, high viral doses can result in delivery to virtually all cells in the liver and transgene expression in a very high proportion (approaching 100%) of hepatocytes (data not shown). Liver, spleen, lung and kidney tissues were treated via two methods. Half of each tissue was snap frozen and sectioned using a cryostat. The other half of the tissue was fixed in 4% paraformaldehyde in 100 mM phosphate buffer (pH 7.4) at room temperature for 4 hours, then transferred to 70% ethanol to stop fixation, embedded in paraffin and sectioned.

The potential involvement of Kupffer cells in limiting effective transduction of hepatocytes was next examined with doxorubicin-containing liposomes ("liposomal doxorubicin"). These liposomes have been reported to deplete Kupffer cells in the liver. See, Daemen et al., *Int. J. Cancer* 61:716-21, 1995; Longman et al., *J. Pharmacol. Exp. Ther.* 275: 1177-1184, 1995; Parr et al., *Biochim. Biophys. Acta.* 1168:249-252. This phenomenon was not observed in Rag-1 mice for reasons that are not understood at present.

Figure 5:
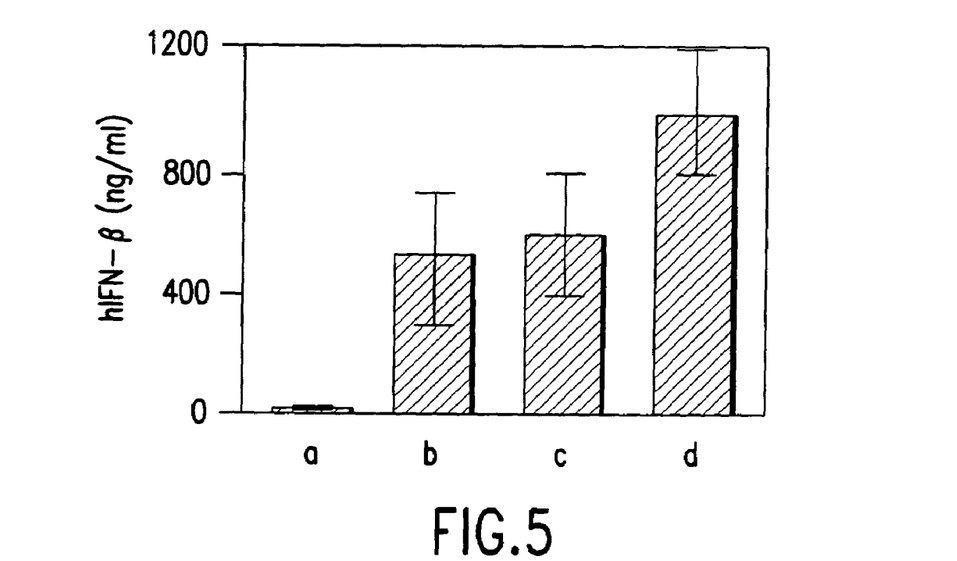
FIG. 5 is a graph showing that depletion of liver Kupffer cells enhances transgene hIFN-β expression.

Intravenous injections of 0.132 μmol/0.1 ml and 0.264 μmol/0.2 ml of liposome-entrapped doxorubicin (100 nm unilamellar liposomes composed of distearoyl-phosphatidyl-choline/cholesterol 55/45 at a drug to lipid molar ratio of 0.2, a gift from Dr. Marcel B. Bally, BC, Cancer Agency) were administered 24 hour prior to the injection of a low dose of H5.110CMVhIFN-β for the temporary depletion of Kupffer cells. As shown in FIG. 5, hIFN-β expression in Balb/c nude mice was evaluated comparing injections of (a) $2 \times 10^{10}$ articles of H5.110CMVhIFN-β alone, (b) $2 \times 10^{10}$ particles H5.110CMVhIFN-β injected 24 h after depletion of Kupffer cells by injection of 0.132 μmol liposome-entrapped doxorubicin, or (c) after depletion with 0.264 μmol liposome-entrapped doxorubicin; or (d) four hours after predosing with $8 \times 10^{10}$ H5.110CMVlacZ. Each strain of mice was injected with the adenoviral constructs as indicated, and sera were collected 24 hour later by terminal bleeding. Treatment of mice with doxorubicin/liposomes prior to administration of $2\times10^{10}$ particles H5.110CMVhIFN-β led to dramatically higher IFN-β expression levels and was nearly equivalent to the effect of high dose H5.110CMVlacZ pre-treatment. The results are shown in FIGS. 4 and 5.

Because fluorescently labeled virus was taken up by the spleen, and in view of the potential of splenic macrophages to sequester virus, the dose response was examined in splenectomized mice. No effect of removing the spleen on reporter expression was observed.

To confirm that the observed enhanced transgene expression was from hepatocytes and to determine whether the Kupffer cells themselves expressed significant levels of the transgene, the H5.110CMVlacZ reporter virus was used. Mice were injected with a range of concentrations of this virus, with or without pre-dosing with the H5.110CMVhIFN-β virus. After 3 days livers were removed and stained for lacZ activity.

As seen upon examination of the resulting tissue sections, tissue staining levels were visually consistent with previous experiments and showed enhanced lacZ staining at even the lowest ($1\times10^{10}$ particles) dose following pre-dosing. When thin sections were examined, it was apparent that the Kupffer cells expressed no detectable lacZ activity, despite their efficient viral uptake, and that the pre-dosing did indeed result in dramatically enhanced hepatocyte expression.

Figure 6:
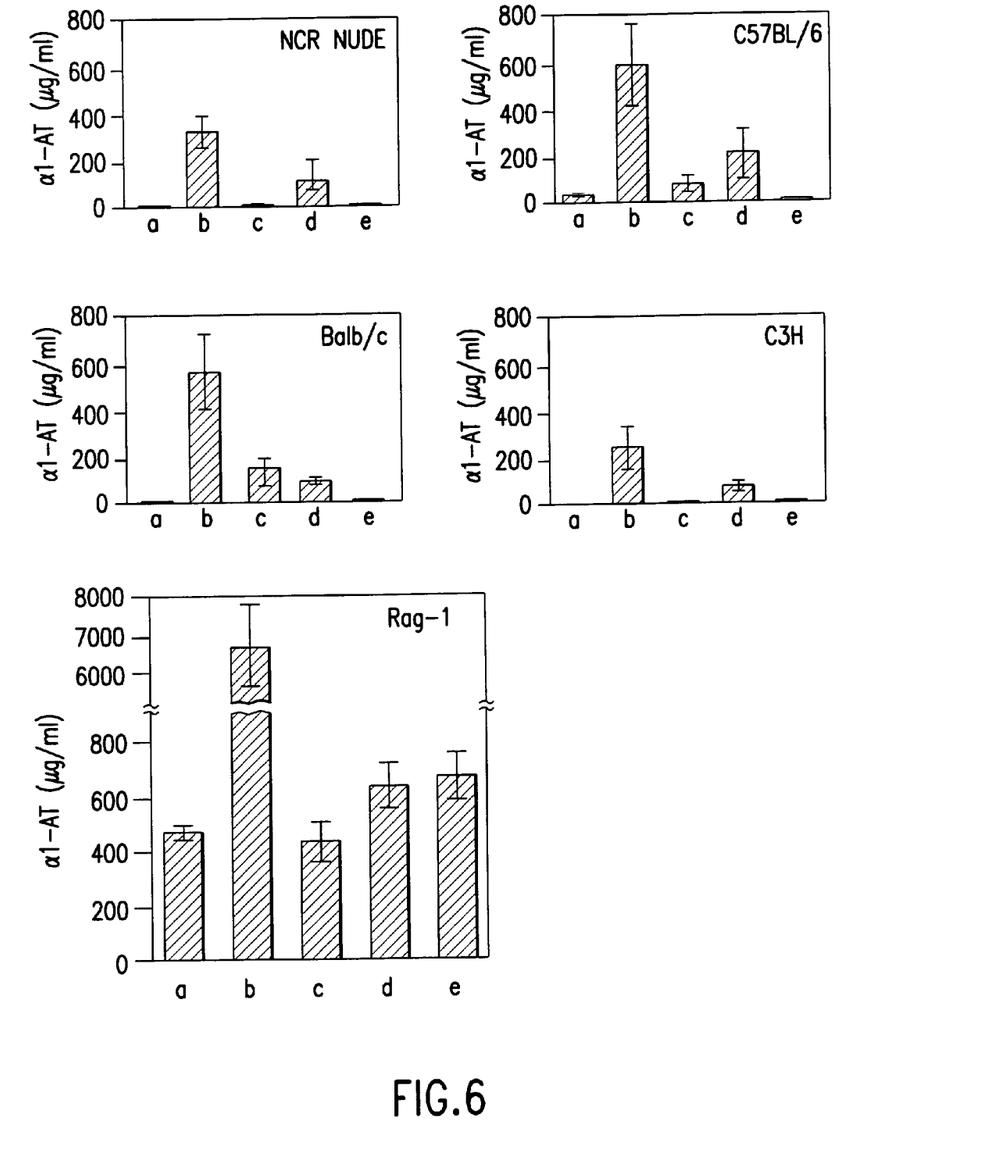
FIG. 6A-6E are graphs depicting mouse strain-specific differences in transgene expression following delivery of H5.010CMVhα1-AT. The mouse strains indicated are FIG. 6A depicting the NCR NUDE mouse strain, FIG. 6B depicting the C57BL/6 mouse strain, FIG. 6C depicting the Balb/c mouse strain, FIG. 6D depicting the C3H mouse strain, and FIG. 6E depicting the Rag-1 mouse strain. The respective strains depicted in FIG. 6A-6E were each injected intravenously with: (a) a low dose ($1\times10^{10}$ particles) of H5.010CMVhα1-AT reporter vector alone, (b) a high dose ($8\times10^{10}$ particles) of H5.010CMVhα1-AT reporter vector alone, (c) $1\times10^{10}$ particles of H5.010CMVhα1-AT coadministered with $8\times10^{10}$ particles of H5.110CMVlacZ (d) $8\times10^{10}$ particles of the H5.110CMVlacZ administered 30 minutes before injection of $1\times10^{10}$ particles of H5.010CMVhα1-AT reporter, or (e) $8\times10^{10}$ particles of H5.110CMVlacZ administered 30 minutes after injection of $1\times10^{10}$ particles of H5.010CMVhα1-AT reporter. ELISA was used to determine serum concentrations of human α1-AT 24 h after viral dosing with injections (a)-(e). The respective injections (a)-(e) are labeled as a-e on the x-axis of the graph for each mouse strain as indicated in FIG. 6A-6E.

The non-linear dose response and the effect of co-administration, pre-treatment or post-treatment with a control adenovirus were tested in five different mouse strains using an adenovirus expressing human α1 antitrypsin (H5.010CMVhα1AT). The results are shown in FIG. 6. Four of the five mouse strains gave essentially similar results with non-linear dosing kinetics and enhancement by co- or pre-administering a non-reporter virus. An 8-fold increase in adenovirus dose resulted in a 102-fold (NCR nude), 228-fold (Balb/c), 160-fold (C3H) and 26-fold (C57BL/6) increase in serum α1AT levels. In all four of these strains of mice, co-administration of H5.010CMVlacZ along with a low dose of H5.010CMVhα1AT increased the resulting α1AT serum levels and pre-treatment with H5.010CMVlacZ gave higher α1AT levels than co-treatment in NCR nude, C3H and C57BL/6 mice. In all four mouse strains, administration of H5.010CMVlacZ after H5.010CMVhα1AT had a minimal effect. There were subtle but reproducible differences between strains, with C57BL/6 giving consistently higher levels of expression at low doses than Balb/c or the nude mice.

Example 6

Non-linear Dose-dependent hIFN-β Adenoviral Transgene Expression is also Observed in Primates Studies were also performed measuring the expression of an adenovirus hIFN-β transgene in rhesus monkeys. Doses were determined by calculating viral particles per body weight. Responses were also measured in mice in these experiments.

Dosages in terms of viral particles per body weight (particles per kg) were calculated assuming a mass of 20 grams per mouse.

Very low to undetectable expression of a virally encoded transgene was observed when $2\times10^{10}$ particles (final dose of $1\times10^{12}$ p/kg) were administered to mice. An approximate inflection point (i.e., a point at which non-linear increase is detected) was observed when $4\text{-}5\times10^{10}$ particles were administered ($2\text{-}2.5\times10^{12}$ p/kg). Very high expression in all mice were observed following administrations of $1\times10^{11}$ particles ($5\times10^{12}$ p/kg).

Similar experiments were also performed in rhesus monkeys (n=3). An approximate inflection point was observed at moderate viral doses of $2\times10^{12}$ p/kg to $4\times10^{12}$ p/kg. Following administration of a moderate viral dose, some monkeys displayed very low expression while others treated at the same dose showed very high levels of expression that were non-linear. In contrast to the results in these moderate dose groups, all monkeys in the low dose group ($1\times10^{12}$ p/kg) displayed very low to undetectable IFN-β expression and all monkeys in the high dose group ($1\times10^{13}$ p/kg) had very high expression which was far greater than a 10-fold increase over the expression levels in the low dose group. This indicates that, in these studies: (1) the inflection point in monkeys is somewhere around the moderate dose, and (2) there is monkey-to-monkey variability in the exact point of the increase.

These results demonstrate that non-linear responses to viral vectors, as monitored by expression of a gene product, are observed in primates as well as mice.

Equivalents

From the foregoing detailed description of the specific embodiments of the invention, it should be apparent that novel compositions and methods involving nucleic acids, polypeptides, and gene therapy and treatment have been described. Although these particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made as a matter of routine for a person of ordinary skill in the art to the invention without departing from the spirit and scope of the invention as defined by the claims. Indeed, various modifications of the invention in addition to those described herein will become apparent to those skilled in the art from the foregoing description and accompanying figures. Such modifications are intended to fall within the scope of the appended claims.

We claim:

1. A method for increasing the level of a therapeutic gene product in a subject, the method comprising administering to said subject
   (a) a first viral vector comprising a therapeutic nucleic acid encoding said therapeutic gene product, wherein said therapeutic gene product is expressed through operable linkage of said nucleic acid to a promoter, and
   (b) an agent that reduces Kupffer cell function, wherein said agent is a second viral vector that does not comprise said therapeutic nucleic acid;
   wherein said second viral vector is the same type as said first viral vector;
   wherein said agent is administered less than 24 hours prior to or concurrently with administration of said first viral vector;
   wherein said first viral vector and said agent are not conjugated;
   wherein said agent is administered by a route selected from the group consisting of direct administration to the liver, intravenous administration, or intraperitoneal administration;
   wherein said first viral vector and said agent reach the liver following administration; and
   wherein levels of said therapeutic gene product are increased in hepatocytes by administration of said agent.

2. The method according to claim 1, wherein said first and second viral vectors are adenovirus vectors.

3. The method according to claim 1, wherein said agent is administered less than 24 hours prior to administration of said, first viral vector.

4. The method according to claim 1, wherein said agent is administered concurrently with administration of said first viral vector.

5. A method for increasing the level of a therapeutic gene product in a subject, the method comprising administering to said subject
   (a) a first viral vector comprising a therapeutic nucleic acid encoding said therapeutic gene product, wherein said therapeutic gene product is expressed through operable linkage of said nucleic acid to a promoter, and
   (b) an agent that reduces Kupffer cell function, wherein said agent is a second viral vector;
   wherein said second viral vector is the same type as said first viral vector;
   wherein said agent is administered prior to, but less than 1 hour prior to, administering said first viral vector;
   wherein said agent is administered by a route selected from the group consisting of direct administration to the liver, intravenous administration, or intraperitoneal administration;
   wherein said first viral vector and said agent reach the liver following administration; and
   wherein levels of said therapeutic gene product are increased in hepatocytes by administration of said agent.

6. The method according to claim 5, wherein said agent is administered less than five minutes prior to administering said first viral vector.

7. The method according to any one of claims 5-6, wherein said first and second viral vectors are adenovirus vectors.

8. The method according to any one of claims 1 or 5-6, wherein said first viral vector is administered by a route selected from the group consisting of oral administration, nasal administration, parenteral administration, transdermal administration, intrabronchial administration, intraperitoneal administration, direct injection into cells, tissue, organ or tumor, intravenous administration, subcutaneous administration, and intramuscular administration.

9. The method according to any one of claims 1 or 5-6, wherein said first and second viral vectors are replication-defective viral vectors.

10. The method according to any one of claims 1, 5-6, or 2, wherein said subject is a primate.

11. The method according to claim 10, wherein said primate is a human.

\* \* \* \* \*